(12) United States Patent
Bohn et al.

(10) Patent No.: US 6,860,268 B2
(45) Date of Patent: Mar. 1, 2005

(54) PEDIATRIC VENTILATION MASK AND HEADGEAR SYSTEM

(76) Inventors: Shelly Bohn, 50 Coventry Way NE., Calgary, Alberta (CA), T3K 5H3; Nancy Quennell, 123 Bow Ridge Crescent, Cochrane, Alberta (CA), T4C 1V2

( * ) Notice: Subject to any disclaimer, the term of this patent is extended or adjusted under 35 U.S.C. 154(b) by 155 days.

(21) Appl. No.: 10/066,562

(22) Filed: Feb. 6, 2002

(65) Prior Publication Data

US 2003/0145859 A1 Aug. 7, 2003

(51) Int. Cl.$^7$ .............................................. A61B 17/00
(52) U.S. Cl. ............................. 128/206.21; 128/200.24; 128/206.26; 128/207.11; 128/207.17
(58) Field of Search ..................... 128/201.22, 201.23, 128/201.24, 201.29, 202.13, 202.19, 203.12, 203.29, 204.18, 205.25, 206.12, 206.21–207.18, 200.14–200.24, 203.16, 205.13; D24/193, 110–110.6; 606/1

(56) References Cited

U.S. PATENT DOCUMENTS

| | | | |
|---|---|---|---|
| D231,803 S | | 6/1974 | Huddy |
| D293,613 S | | 1/1988 | Wingler |
| 4,848,334 A | * | 7/1989 | Bellm .................... 128/207.11 |
| 4,989,596 A | * | 2/1991 | Macris et al. .......... 128/201.28 |
| 5,038,776 A | | 8/1991 | Harrison et al. |
| D323,908 S | | 2/1992 | Hollister et al. |
| 5,121,745 A | | 6/1992 | Israel |
| 5,243,971 A | | 9/1993 | Sullivan et al. |
| 5,429,126 A | | 7/1995 | Bracken |
| 5,441,046 A | | 8/1995 | Starr et al. |
| D362,061 S | | 9/1995 | McGinnis et al. |
| 5,505,207 A | | 4/1996 | Abbs et al. |
| 5,542,128 A | | 8/1996 | Lomas |
| 5,570,689 A | | 11/1996 | Starr et al. |
| 5,647,357 A | | 7/1997 | Barnett et al. |
| 5,657,752 A | | 8/1997 | Landis et al. |
| 5,690,096 A | | 11/1997 | Burch |
| 5,746,201 A | | 5/1998 | Kidd |
| 5,813,423 A | | 9/1998 | Kirchgeorg |
| 5,853,002 A | | 12/1998 | Kawasaki |
| 5,884,624 A | | 3/1999 | Barnett et al. |
| 5,921,239 A | * | 7/1999 | McCall et al. .......... 128/205.25 |

(List continued on next page.)

FOREIGN PATENT DOCUMENTS

DE     197 35 359 A1     1/1999

OTHER PUBLICATIONS

A2ZZ NewZzz Briefs—Comfort Classic Nasal Mask—no date.

(List continued on next page.)

*Primary Examiner*—Glenn K. Dawson
(74) *Attorney, Agent, or Firm*—Sean W. Goodwin; Linda M. Thompson

(57) ABSTRACT

A nasal or full-face mask and headgear system for improving pediatric compliance of ventilation therapy, including CPAP or BiPAP, and sized for pediatric use is provided. Each mask has a shallow concave rigid shell bearing the visage of a caricature. Unique caricatures are predetermined to represent different sizes of masks. Further, headgear is provided in keeping with the caricature theme and having additional aspects such as ears, removably attached to it. Each mask has an inner inflatable cuff to improve fit and an outer replaceable cuff to facilitate cleaning as well as fitting. The headgear is attached to the mask at three contact points using straps having key slots attached to ends of the straps and raised buttons on the mask shell. The straps are adjustable for length using Velcro™ and are not adjusted each time the system is placed onto the patient, improving positioning of the mask when the patient is asleep or resistant.

32 Claims, 7 Drawing Sheets

U.S. PATENT DOCUMENTS

| | | | |
|---|---|---|---|
| D420,128 | S | 2/2000 | Hoenig |
| 6,019,101 | A | 2/2000 | Cotner et al. |
| 6,035,852 | A | 3/2000 | Hoftman |
| 6,095,647 | A | 8/2000 | Cook |
| 6,112,746 | A | 9/2000 | Kwok et al. |
| 6,119,693 | A | 9/2000 | Kwok et al. |
| 6,119,694 | A | 9/2000 | Correa et al. |
| 6,192,876 | B1 * | 2/2001 | Denyer et al. ......... 128/205.25 |
| 6,192,886 | B1 | 2/2001 | Rudolph |
| D441,860 | S | 5/2001 | Kopacko et al. |
| D448,473 | S | 9/2001 | Barnett et al. |
| 6,405,725 | B1 * | 6/2002 | Christopher ........... 128/200.26 |
| 6,505,351 | B2 * | 1/2003 | Yeh ............................... 2/206 |
| 6,615,832 | B1 * | 9/2003 | Chen ..................... 128/206.26 |
| 2001/0032648 | A1 | 10/2001 | Jestrabek-Hart |

OTHER PUBLICATIONS

Morielli et al—Treatment of sleep–disordered breathing in children with myelomeningocele—Pub Med website—Pediatr Pulmonol Dec. 2000;30(6):445–52.

Guilleminault et al. Home nasal continuous positive airway pressure in infants with sleep–disordered breathing. The Journal of Pediatrics Dec. 1995; 127(6): 905–912.

McNamara et al. Effects of nasal continuous positive airway pressure on apnoea index and sleep in infants. J. Pediatr. Child Health 1995 (31), 88–94.

Marcus et al. Use of nasal continuous positive airway pressure as treatment of childhood obstructive sleep apnea. J Pediatr 1995;127:88–94.

Waters et al. Obstructive Sleep Apnea: the Use of Nasal CPAP in 80 children. AM J Respir Crit Care Med 1995;152:780–785.

McNamara et al. Effects of nasal CPAP therapy on respiratory and spontaneous arousals in infants with OSA. J Appl Physiol. 1999;87(3):889–896.

Guilleminault et al. Chronic snoring and obstructive sleep apnea syndrome in children. Lung 1990 Suppl:912–919.

Committee of the Scientific Assembly on Pediatrics. Standards and indications for cardiopulmonary sleep studies in children. Am J Respir Crit Care Med 1996;153:866–878.

Kirk et al. Diagnostic approach to obstructive sleep apnea in children. Sleep Medicine Reviews 1998; 2(4):255–269.

Jarund et al. Treatment of sleep apnoea with continuous positive airway pressure in chlidren with craniofacial malformations Scan J Plast Recontr Hand Surg 1999;33:67–71.

Carole Marcus. Sleep–disordered breating in children. Am J Respir Crit Care Med 2001;164:16–30.

McNamara et al. Obstructive sleep apnea in infants and its management with nasal continuous positive airway pressure. Chest 1999; 116:10–16.

Roscoe Medical www.roscoemedical.com/catalog/cpap-mask.htm.

Respertise Pulmonary Services Inc. www.respertise.com/products.html.

Respertise Pulmonary Services Inc. www.respertise.com/cpapheadgear.html.

Tiara Medical Systems Inc. www.tiaramed.com/prod01.htm.

Tiara Medical Systems Inc. www.tiaramed.com/prod02.htm.

Sunrise Medical www.sunrisemedical.com/products/produc_list.jsp?FOLDER%3%3Efolder.

CPAP Company www.cpap–company.com/ 1–877–348–2727/bubbles.htm.

* cited by examiner

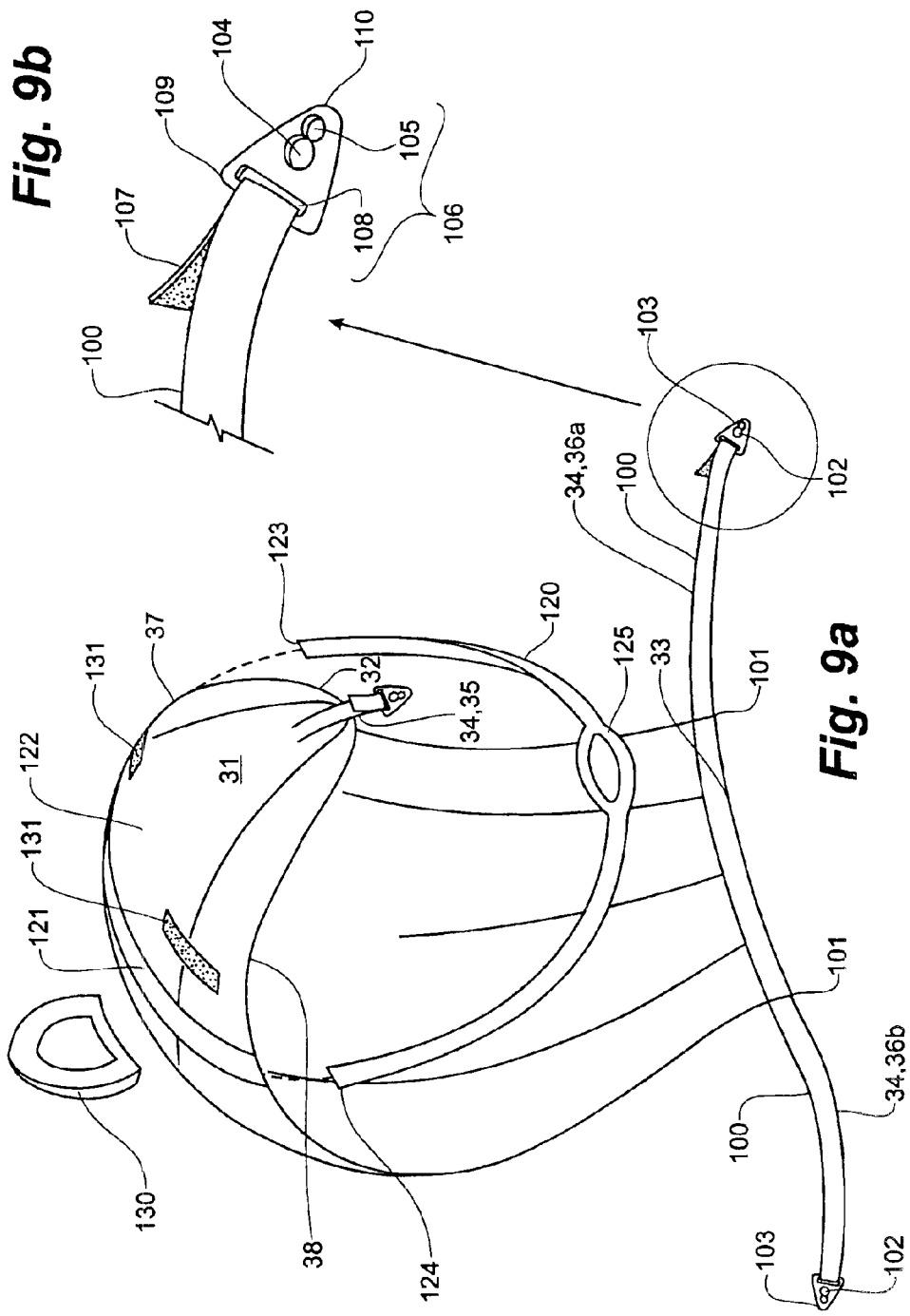

PEDIATRIC VENTILATION MASK AND HEADGEAR SYSTEM

FIELD OF THE INVENTION

The present invention relates to apparatus used in the field of non-invasive and invasive ventilation therapies including continuous positive airway pressure (CPAP) or bi-level positive air pressure (BiPAP) therapy and particularly to nasal and full-face masks and headgear used to treat pediatric patients.

BACKGROUND OF THE INVENTION

Continuous positive airway pressure (CPAP) or alternatively, Bilevel Positive Airway Pressure (BiPAP) have become conventional forms of non-invasive ventilation treatment for adult patients suffering from obstructive sleep apnea and other nocturnal breathing disorders. Furthermore, not only has it been shown to be an effective therapy, but there is also evidence that it contributes to less time in hospital, fewer medical complications and decreased mortality compared to immediate intubation and ventilation.

Continuous positive airway pressure (CPAP) is delivered by a positive airway pressure generator into a mask worn by the patient while sleeping. This effectively dilates the upper airway, preventing its collapse, thus enabling the patient to assume a normal breathing pattern which results in an uninterrupted sleep. For many patients this therapy dramatically improves their daytime functioning and behaviour as well as their general health.

BiPAP delivers CPAP but also has the capability to sense when an inspiratory effort is being made by the patient and, in turn, delivers a higher pressure during inspiration. When flow stops, the pressure returns to the CPAP level. This positive pressure wave during inspirations unloads the diaphragm, decreasing the work of breathing and has been found particularly useful in patients with chronic respiratory failure due to neuromuscular weakness or dysfunction or chest wall abnormalities.

One study showed that the use of CPAP has resulted in a reduction of intubation from 74% to 16%, major complications were decreased from 48% to 16% and length of stay in hospital was reduced from 35 days to 23 days. Mortality was decreased from 29% to 9%. There is also evidence from randomized, controlled trials to show that CPAP improves oxygenation, hypercapnia and reduces the rate of endotracheal intubation in pulmonary edema.

More recently, CPAP has become a therapy of choice for pediatric patents suffering from abnormal breathing during sleep resulting from among others, small upper airways, upper airway resistance syndrome, persistent obstruction following surgery for adenotonsillar hypertrophy, craniofacial anomalies, neuromuscular weakness, obesity, spina bifida and Down's Syndrome. In many cases, standard invasive respiratory intervention such as tracheostomies and intubation can be avoided. Sleep apnea has also been reported in infants considered to be at risk of death from sudden infant death syndrome (SIDS) and has been seen in infants who have subsequently died of SIDS.

Much of the information relating to compliance problems associated with CPAP are reported from adult studies. Clearly, adults are better able to provide feedback to health care providers, regarding those issues which prevent or limit their ability or desire to utilize the therapy. It can be extrapolated however, that these issues are also present for the pediatric patient and, in many cases, are made worse due to the patient's lack of understanding of the therapy and fear of intervention, as well as the commercial unavailability of a wide variety of sizes or well fitting masks and headgear.

The major reported obstacle for most adult patients to overcome is becoming accustomed to the ventilation system. Approximately 20% of patients, for a variety of reasons, never learn to tolerate it and a substantial proportion of the others have a hard time using it regularly. The statistics for use in pediatric patients can be much worse. Kribbs et al. reported in the American Journal of Respiratory Diseases in 1993 that only 6% of the 35 CPAP patients studied used CPAP 70% of the time for 7 hours or greater, suggesting that frequent, long duration usage of nasal CPAP is a rare occurrence in obstructive sleep apnea (OSA). Efforts to enhance CPAP and BiPAP use are needed especially early in treatment to reduce the significant nature of the disorder and death associated with OSA and nocturnal hypoventilation. Problems such as mask fit, pressure sores or redness around the nose and nasal dryness or stuffiness are common reasons that patients fail to comply. Most of these problems are solvable by finding a mask that fits properly.

Air leaking from around a poorly fitting nasal mask can be quite uncomfortable and possibly result in suboptimal treatment. Air leaking causes the generator to blow more air to achieve the prescribed pressure, thus making it more uncomfortable for the patient and possibly causing more arousals during sleep. In many cases, the air is directed from the poorly fitting mask directly into the patient's eyes. For this reason, it is essential that the mask fit properly, which is particularly challenging in the case of children. Further, as the patient drifts off to sleep, the jaw tends to relax and the mouth may open. When this happens, air from the generator may escape through the mouth. A properly fitting chin strap can assist in keeping the mouth closed during sleep.

Headgear is used to hold the mask in place over the nose, or over the nose and mouth, in the case of a full-face mask. Typically, headgear comprises a plurality of straps connected to the mask, which extend about the head or to a cap fitted on the head, to stabilize the mask.

Pediatric patients may be introduced to CPAP from the time of birth and may continue to require treatment throughout their entire lives. Clearly nasal and full-face masks designed to fit the adult face are unsuitable for these patients, especially in their early years. Craniofacial abnormalities may add to the difficulty in finding a mask that fits well. Further, it has been reported that children wearing an improperly fitting mask during bone development can develop facial abnormalities as a result of the poorly fitting mask.

Nasal prongs or nasopharyngeal tubes, that may be used in a hospital setting to deliver CPAP, are not available for equipment designed for the home environment. As well, most manufacturers provide only one size of mask for pediatric patients, if they provide a pediatric mask at all. Currently, to Applicant's knowledge there are no masks marketed as "pediatric masks" that are small enough to fit premature neonatal patients satisfactorily. It appears that there is little recognition that a unique range of sizes is required for the pediatric population, which extends, in age, from neonate to pre-teen. Patients who have syndromes that result in stunted growth may require pediatric sized masks throughout their lives.

Currently, masks and headgear may be sold as a prepackaged system, however, a mask from one system may be better suited with the headgear from another, for a particular patient. Costs escalate if pre-packaged systems are purchased, but only one of the components is usually used, due to fit or comfort considerations, in combination with a component from another system. Often, a suitable component is not available at all and the therapist and patient must "make do" with the closest alternative, which is often uncomfortable and heavy and as a result little used.

One system intended specifically for pediatric use, known to Applicant, is the Resmed Infant Mask System having a nasal mask and a cap (RESCAP™). Resmed is an Australian Corporation. A single strap extends from a point at the front of the cap to a tab extending from the top of the mask, between the eyes, which acts as a forehead support and has a cushion designed to rest against the forehead to reduce pressure sore formation. A second strap extends through the forehead support and around the patient's head to the sides of the cap. Third and fourth straps extend from protruding tabs at the sides of the mask to join the cap adjacent it's bottom edge. The straps are attached to the mask and to the cap using Velcro™.

A single, flexible cuff is formed about the nasal mask to accommodate and seal about the nose. While the mask is small enough to fit some pediatric patients, the cuff must often be retrofit or cut to fit over individual patient's noses. Once the cuff has been cut to provide a better fit for slightly larger noses or abnormalities, the cut edges are likely to cause irritation at the points of contact or leaks where there is insufficient sealing. Further, the cushioned forehead support continues to cause pressure sores, especially in the smallest of the patients where the headgear may not fit adequately and the mask moves about. The mask shell is generally triangular in shape and has a flat surface into which a port is formed and tubing is attached. For many patients, the flat surface of the mask shell does not permit adequate space for the nose and as a result the nose rests against the surface often resulting in pressure sores.

Many of the pediatric patients are non-compliant and may fall asleep periodically throughout the day and night. The Velcro™ fasteners are difficult to adjust without arousing the child. More importantly, if the child has fallen asleep in an awkward position, it is difficult to ensure that the mask is positioned correctly and snuggly on the face, as the length of the straps are dependant on where the fasteners are fastened each and every time the mask is worn.

Typically, patients introduced to CPAP at the toddler stage of development, exhibit great resistance to use of the mask. At least in part this resistance develops because of comfort issues, including size which may obstruct their vision, pressure sores as a result of contact points on the forehead and cheeks, excessive weight or, in some cases, latex allergies and may further include psychological reasons. Many of these patients have spent considerable time in institutions, such as hospitals, and have been subjected to almost constant medical intervention of one type or another. Placing a mask on the face may elicit fear of the apparatus itself or what it is perceived to be associated with and particularly for those who have become tactile defiant, compliance becomes a struggle that many parents and therapists are unable to resolve.

Often psychologists are included as an integral part of the therapy team as they attempt to improve the pediatric patient's compliance with CPAP or BiPAP therapy. In some cases, all members of a family are encouraged to also wear a mask while preparing the patient and their siblings for bed so that the patient views it as a "normal" process in the bedtime ritual. The mask may be included among a child's toys so that they come to see it as something fun rather than a medical device. Games are created around the issue of wearing the mask. Often several months are spent in this process during which little or no therapy is actually occurring. For some patients, the loss of time may be critical to their overall health and may result in the need to proceed to more conventional invasive techniques such as tracheostomy, without giving the therapy a chance.

One product used to improve nebulizer compliance in asthmatic children is the "Bubbles The Fish" pediatric aerosol mask for use with a PARI nebulizer. The mask is transparent, but made to look like a fish face so that children find it fun to use, greatly improving compliance. The aerosol mask however, cannot be used to administer CPAP, as it is designed to be hand held over the nose and mouth for short-term use for inhalation only, rather than attached to headgear for continuous use. Size and configuration are less important for this type of therapy, typically requiring only a "one size fits all" mask.

The range of mask and headgear sizes required for the pediatric population may represent very small incremental and visually indistinct changes in dimensions. For this reason it is desirable to have a system for simple recognition of the different sizes available, especially when systems are further obscured when pre-packaged.

Clearly, there is a need for a ventilation mask and associated headgear that is available to fit pediatric patients ranging from the tiniest of neonates to those nearly able to wear small adult sized apparatus. Such a system would be comfortable, viewed as something desirable to wear by the patient and readily identifiable as to its size for ease of fitting.

SUMMARY OF THE INVENTION

The mask and headgear system of the present invention alleviates the problems associated with patient compliance during ventilation therapy such as CPAP or BiPAP therapy. The caricatures represented on both the mask shell and on the headgear create a fun, readily accepted apparatus that is not viewed by the pediatric patient as merely another intrusive medical device.

Further, the association of each unique caricature with a particular predetermined size assists the therapist in rapid identification and fitting of the mask and headgear to the patient. This is of particular advantage when a wider range of pediatric sized masks are provided for improving fit-matching and which may only differ by small increments that are not readily discerned visually. Further, proper size selection improves comfort and fit with increased likelihood of compliance.

In a broad aspect, the invention is a system for improving compliance in a pediatric population for the use of continuous positive or bi-level airway pressure masks and headgear and providing size recognition comprising: a plurality of masks and headgear of predetermined known matched and serial sizes so as to fit a range of pediatric patients; and a size indicator being a predetermined visage of a caricature represented on each of the plurality of masks, each caricature being predetermined to represent one of each of the plurality of sizes. More particularly, the size indicator is the visage of a caricature, such as an animal, on the shell of the mask and related aspects such as ears, in keeping with the caricature, are attached to the headgear.

More preferably, the invention comprises a unique mask having a concave shell which is suitable for fitting over the nose or nose and mouth of a pediatric patient. The concave profile of the shell permits sufficient room for the patient's nose so that it does not rest on the shell, reducing the incidence of pressure sores. Further, the concave shape permits greater air movement without an increase in dead space within the interior of the mask.

The mask provides both an outer replaceable cuff and an inner inflatable cuff. The outer cuff protects the inner cuff from contact with the patient's face and can be easily removed for cleaning or replacement with a cuff having a different size of opening for the nose or nose and mouth. The inner cuff can be inflated to varying degrees to provide a wider range of profiles suitable for sealing against individual patient's faces to provide an optimum fit within a single mask size. The inner cuff when inflated, positions the shell further away from the patient's nose and cheeks allowing more room for the nose. Further, in patients such as those with Down's Syndrome, in which there is relatively little, if any, nasal bridge, inflation of the interior cuff aids in preventing the mask from slipping up towards the patient's forehead. When deflated, the mask has a flatter profile, the shell being positioned closer to the nose and cheeks, for permitting a better fit for individual patients.

The above apparatus and methodology enables the provision of a mask and a system which is particularly useful in the treatment of pediatric cases. Accordingly, a broad system is provided for improving compliance in a pediatric population for the use of ventilation masks and headgear and providing size recognition comprising: a plurality of masks and headgear of predetermined known matched and serial sizes so as to fit a range of pediatric patients wherein the mask further comprises a concave shell; at least one flexible cuff attached about a periphery of the shell and having an opening for receiving a patients nose or nose and mouth; a port in the shell for receiving tubing for attachment to a ventilation device; at least one exhalation port; and means for attachment to the headgear; and the headgear comprises a cap and a plurality of straps having means for attachment to the mask; and a size indicator being a predetermined visage of a caricature, preferably animals, represented on each of the plurality of masks, each caricature being predetermined to represent one of each of the plurality of sizes.

Such a mask for improving compliance in a pediatric population would comprise: a concave shell having an outer periphery and having a size selected from a plurality of predetermined sizes; at least one flexible cuff attached to the shell about the periphery and having an opening so as to receive a patient's nose or nose and mouth; at least one port in the shell for receiving tubing; at least one exhalation port; and a size indicator, the indicator being indicia representing one of a plurality of caricatures, each caricature predetermined to represent one of the plurality of predetermined sizes.

Particularly where fit is an issue, the mask comprises a concave shell having an outer periphery; a flexible exterior cuff attached to the shell about the periphery and having an opening so as to receive a patient's nose or nose and mouth; an inflatable interior cuff attached to the shell and positioned inside the exterior cuff, the inflatable cuff further comprising a valve port extending through the shell and in fluid communication with the inflatable cuff; at least one exhalation port; and at least one port in the shell for receiving tubing.

BRIEF DESCRIPTION OF THE DRAWINGS

FIG. 9a is a perspective view of a headgear of the present invention, without a mask attached; and FIG. 9b is a close-up perspective view of the end piece and key slot of a headgear strap.

DETAILED DESCRIPTION OF THE PREFERRED EMBODIMENT

Figure 1:
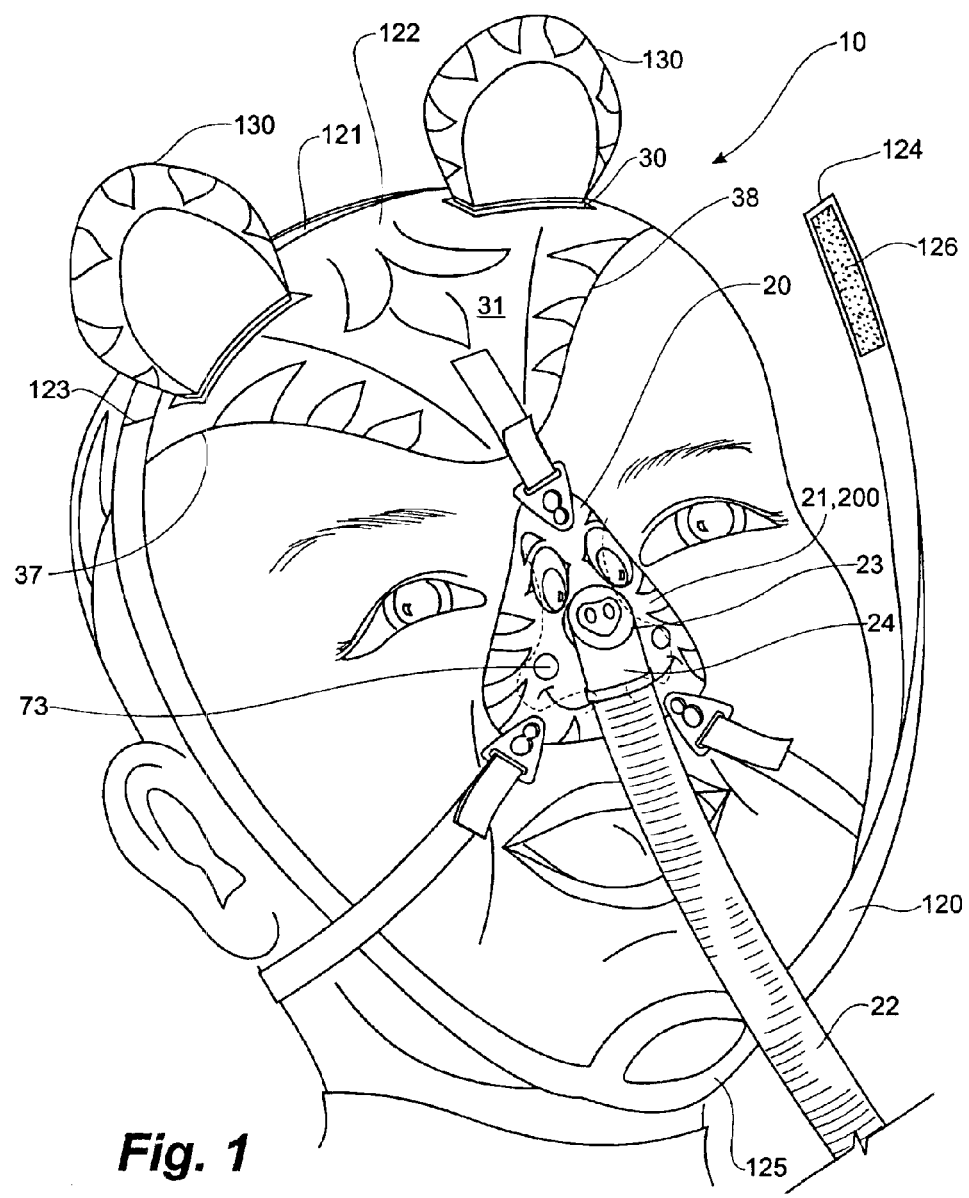
FIG. 1 is a perspective view of a nasal mask, fit over the nose of a patient, and headgear of the present invention having an animal face portrayed on the mask and including the optional matching ears on the headgear including an optional chin strap.

Having reference to FIG. 1, a CPAP mask and headgear system 10 of one embodiment of the invention is shown. The nasal mask 20 comprises a shallow concave rigid shell 21, bearing the visage of a caricature 200, for positioning over the nose of a pediatric patient. The mask 20 is held in place over the patient's nose by headgear 30, worn by the patient. The mask 20 is connected to a ventilation device (not shown), such as a non-invasive CPAP or BiPAP machine or an invasive device such as a respirator, by tubing 22 extending from a port 23 in the mask 20 through which air pressure is administered to the patient. A swivel 24 having a right angle bend is fitted in rotatable, sealed arrangement about the port 23 in the shell 21 for attaching the tubing 22 to the shell 21. The swivel 24 is freely rotatable about the port 23 to permit movement of the tubing 22 without displacing the mask 20 from the patient's face. Further, the swivel 24 is bent at a right angle to prevent the tubing 22 from extending directly outward from the mask 20 where it may become a hindrance or highly visible to the patient.

Figure 2:
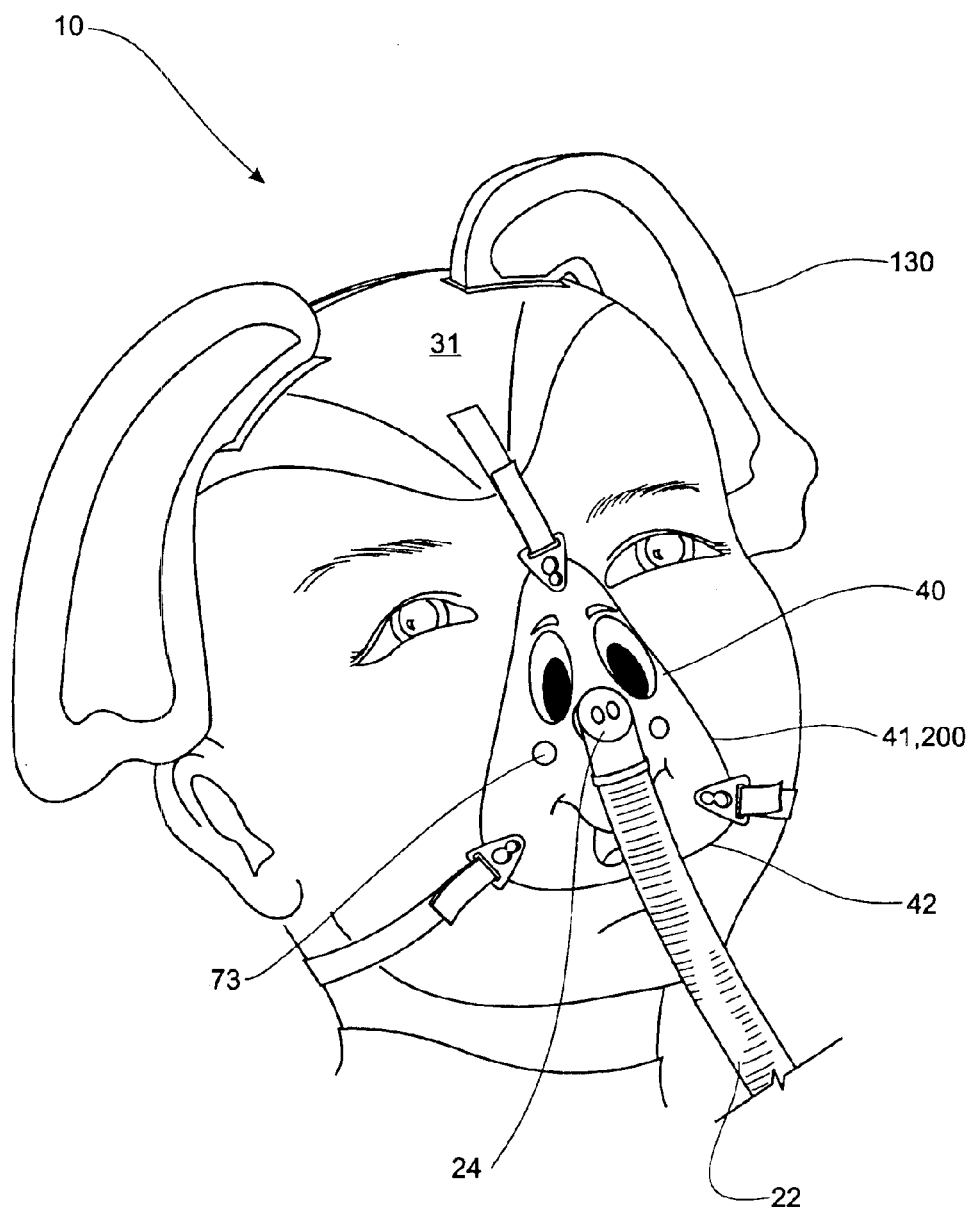
FIG. 2 is a perspective view of a full-face mask of the present invention, the mask fit over a patient's nose and mouth.

Similarly, FIG. 2 shows a full-face mask 40 used to cover both the nose and the mouth of patients who are unable to breath solely through the nose. The shell 41 of the full-face mask 40 is elongated to cover the nose and mouth and may be slightly wider at a bottom edge 42 than a nasal mask 20 used for the same sized patient.

The shells 21, 41 are concave in shape so as to permit adequate space for the patient's nose without having the nose impinge upon the shell 21.

Figure 3C:
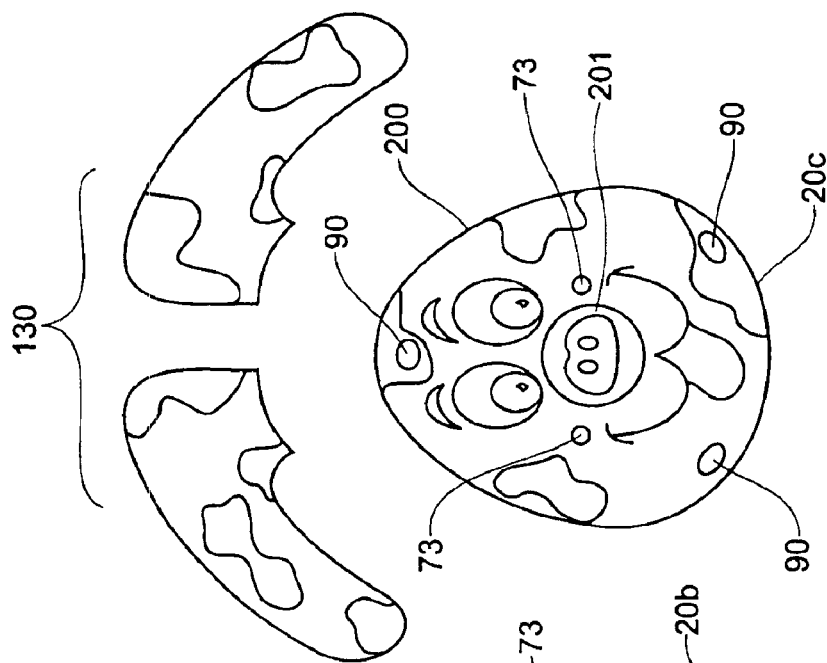
FIGS. 3a–3c are front views of a series of nasal masks, each mask having a different size, the sizes represented by different caricatures.
Figure 3B:
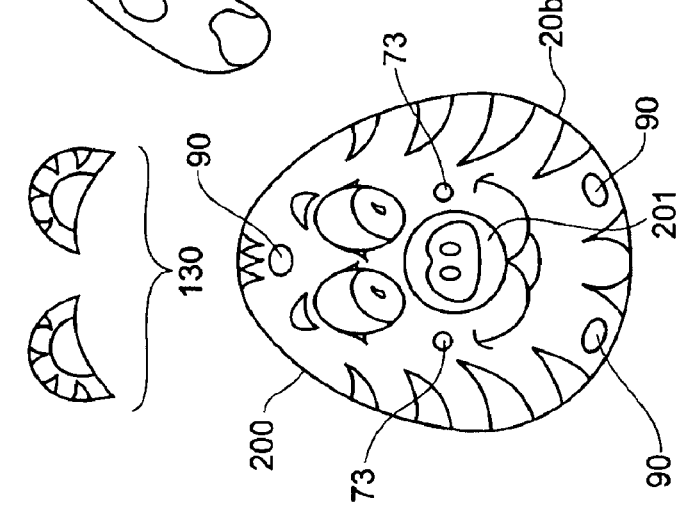
Figure 3A:
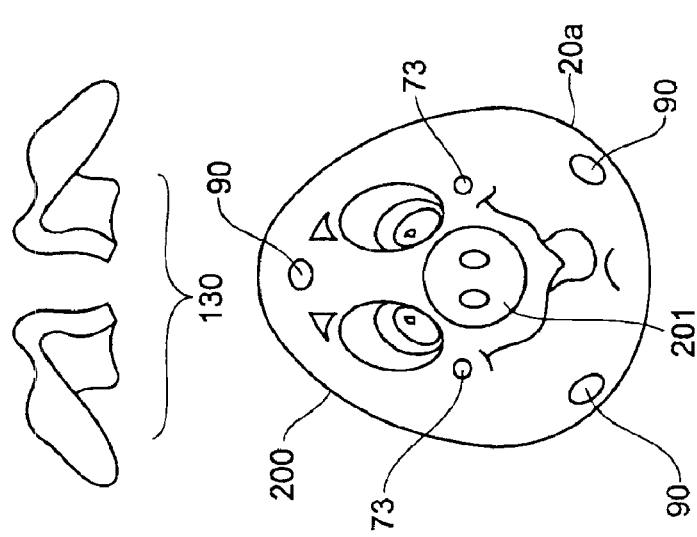
Figure 4A:
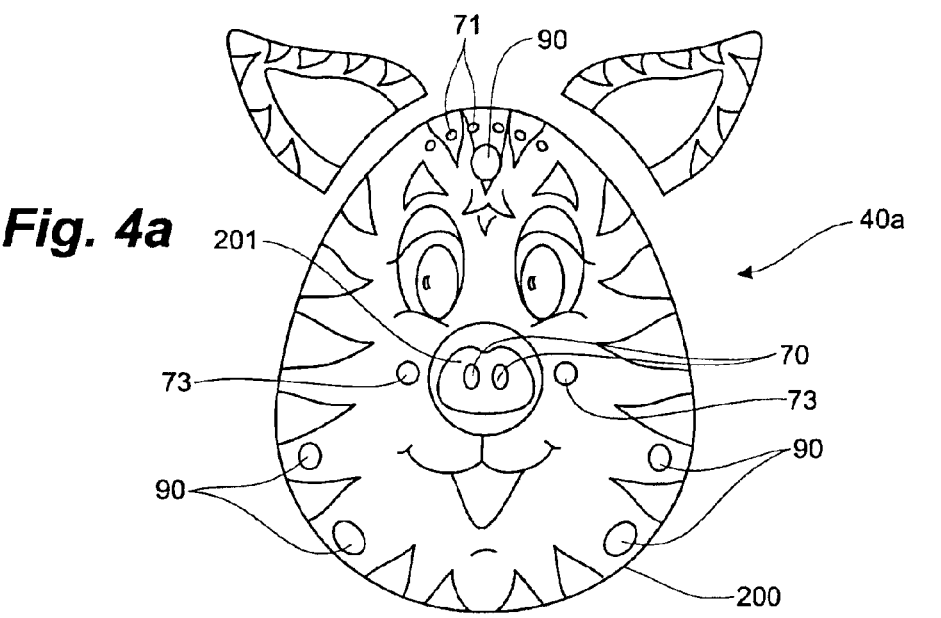
FIGS. 4a and 4b are front views of a series of full-face masks, each mask having a different size, the sizes represented by different caricatures.
Figure 4B:
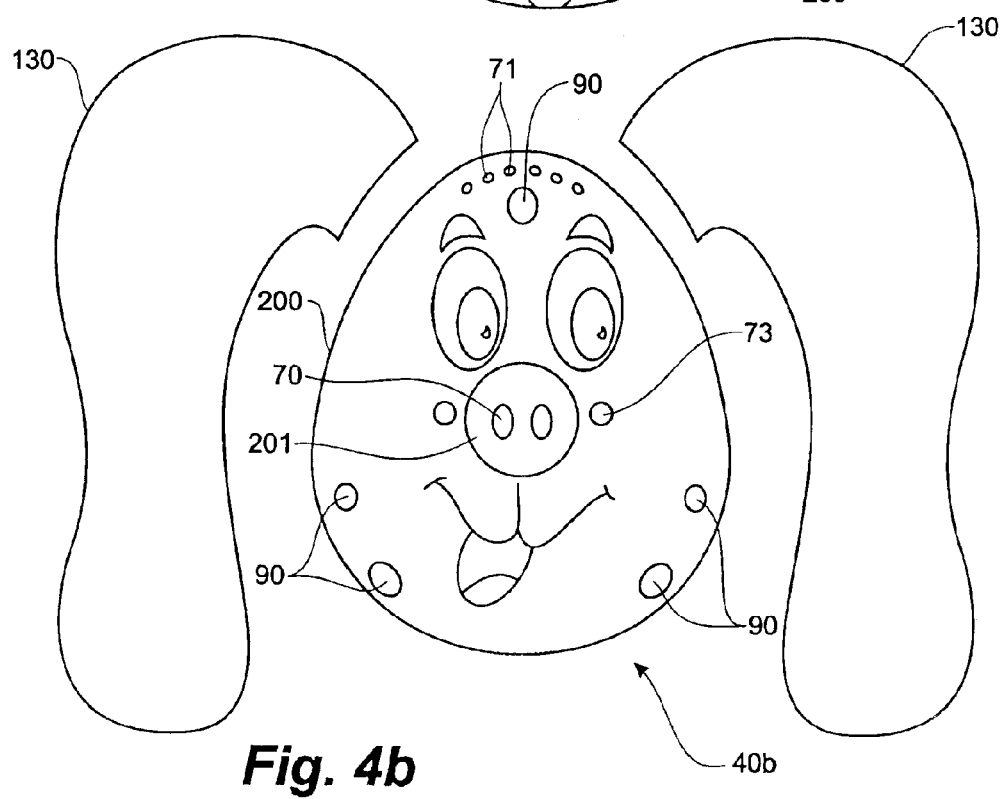

FIGS. 3 and 4 illustrate a representative range of nasal 20 and full-face 40 mask sizes required for fitting a pediatric population ranging in age from newborn until the patient fits known adult masks. Size variations, small 20a, medium 20b and large 20c, shown in FIG. 3, and small 40a and large 40b, shown in FIG. 4, are often not readily discernable at a first glance and may be especially difficult to identify when the systems 10 are packaged for shipping. Accordingly, the application of a unique caricature 200 on each sized mask 20,40, to reference a particular predetermined size, makes it easy to readily select the size appropriate for the patient, at a glance.

Figure 5A:
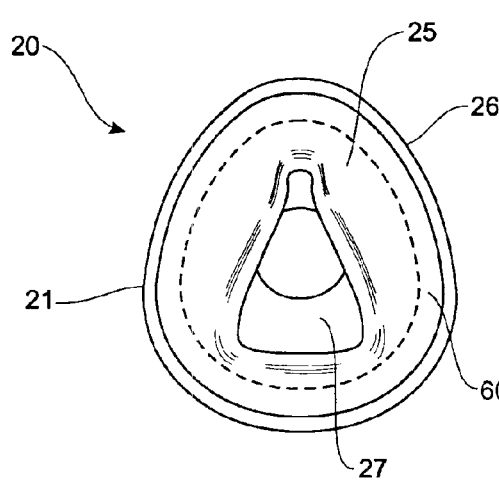
FIG. 5a is a back view of a nasal mask having a replaceable exterior cuff and an inflatable inner cuff.
Figure 5B:
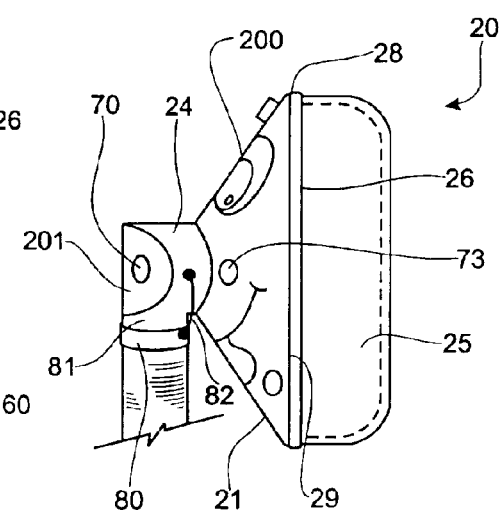
FIG. 5b is a side view of a nasal mask according to FIG. 5a showing extension of the cuff from a profile of a mask shell having an attached swivel and tubing.

Having reference to FIGS. 5a and 5b, each nasal mask 20 further comprises a first external flexible cuff 25 attached to a periphery 26 of the shell 21 for providing a seal between the shell 21 and the patient's nose and cheeks. An opening 27 is formed in the cuff to permit the nose to protrude therethrough into the shell 21. Preferably, the external cuff 25 is removably attached, so as to permit removal for cleaning and replacement with cuffs 25 having larger or smaller openings 27 to further ensure an optimum fit for the patient.

Figure 6A:
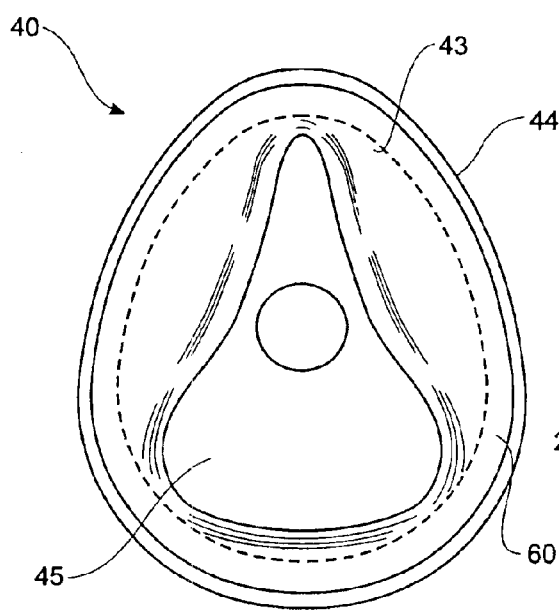
FIG. 6a is a back view of a full-face mask having a replaceable exterior cuff and an inflatable inner cuff.
Figure 6B:
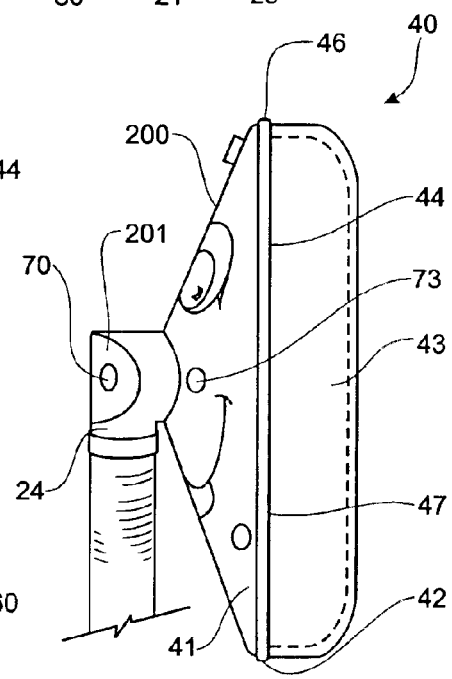
FIG. 6b is a side view of a full-face mask according to FIG. 6a showing extension of the cuff from the profile of a mask shell having an attached swivel and tubing.

FIGS. 6a and 6b show a full-face mask 40, having a similar external cuff 43 attached about a periphery 44 of a full-face shell 41, however an opening 45 in the external cuff 43 is sized to fit over both of the patient's nose and mouth.

Figure 7:
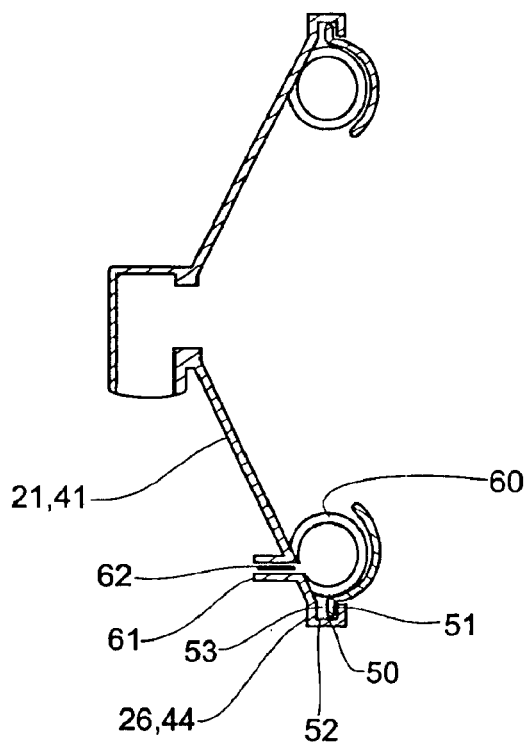
FIG. 7 is a partial cross-sectional view of an inflatable inner cuff and a replaceable outer cuff attached to the mask shell.

In a preferred embodiment of the invention and having reference to FIG. 7, a lip 50 protrudes about the periphery 26,44 of the shell 21, 41 under which an outer compressible edge 51 of the exterior cuff 25, 43 is trapped. A thickness 52 at the compressible edge 51 of the exterior cuff 25,43 is slightly larger than a space 53 between the lip 50 and the shell 21,41. The cuff edge 51 is compressed into the space 53 and is thus retained therein. The external cuff 25, 43 can be readily removed by pulling the compressible edge 51 out of the space 53.

More preferably, as shown in FIGS. 5a, 6a and 7, a second non-removable interior cuff 60 is formed about each shell's periphery 26, 44, positioned inside the exterior cuff 25,43. The interior cuff 60 is inflatable, permitting additional adjustment of the fit between the mask 20, 40 and the patient's face. A small valve port 61 extends outward from the shell 21,41 and is in fluid communication with the interior cuff 60 so as to permit air to be injected, typically using a syringe (not shown), into the inflatable cuff 60 until it is suitably inflated to fit the patient. Similarly, the interior cuff 60 can be deflated, by depressing a valve stem 62 within the valve port 61, much like an inner tube in a vehicle tire, if a flatter profile is required for fitting.

Advantageously, when inflated, the inflatable cuff 60 moves the exterior cuff 25,43 outward into contact with the patient's face. Therefore, it is only the replaceable exterior cuff 25,43 that is subjected to facial oils, medications and the like, present on the patient's face. When the exterior cuff 23, 45 requires cleaning or replacing it can simply be pulled from the lip 50 and replaced.

As shown in FIGS. 3a–3c, 4a, 4b, 5b and 6b, each shell 21,41 further comprises exhalation ports 70 to prevent re-breathing of $CO_2$ rich exhalation air. Preferably, the exhalation ports 70 are formed in the swivel 24, directly adjacent the patient's nose. More preferably, in the case of the full-face mask 40, a plurality of small perforations 71 about the periphery of the full-face shell 41 act as additional exhalation ports 70, so as to further prevent re-breathing of $CO_2$, when both the nose and mouth are covered.

More preferably, the exhalation ports 70 formed in the swivel 24 add to a nasal feature 201 of the caricature 200.

Optionally, the shells 21, 41 comprise at least one additional port 73 having a cap (not shown) for entrainment of additional inhalation gases, such as oxygen or for measurement of parameters such as end tidal $CO_2$ for monitoring excess $CO_2$ re-breathing.

Preferably, as shown in FIG. 5b, a retaining ring 80 is fit about a bottom portion 81 of the swivel 24 and is axially moveable thereon. The retaining ring 80 is slightly larger in diameter than the swivel 24 and is retained on the swivel 24 by a flexible attachment 82. The retaining ring 80 is moved axially downward over an outside of the tubing 22, when the tubing 22 is slipped over the swivel's bottom portion 81, applying compression to retain the tubing 22 on the swivel 24.

Figure 8:
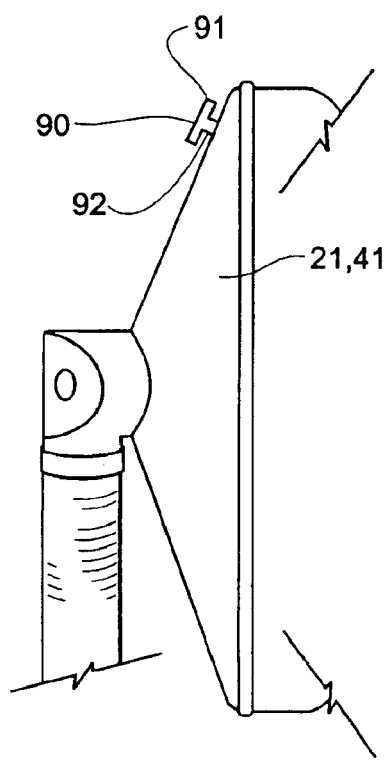
FIG. 8 is a close up side view of the raised buttons attached to the mask shell for attachment of headgear straps.

As shown in FIGS. 3 and 4, a plurality of raised buttons 90 are formed at a top 28, 46 and sides 29, 47 of each shell 21,41 for attachment of the headgear 30. As shown in FIG. 8, each button 90 comprises a large shaped head 91 supported on a smaller shank 92 attached to the shell 21,41.

Preferably, in the case of the larger full-face mask 40, more than one raised button 90 is located on each side 47 of the full-face shell 41 to enhance customized fitting of the system 10.

Having reference to FIGS. 1, 2, 9a and 9b, the headgear 30 is shown. The headgear 30 is used to position the nasal or full-face mask 20, 40 correctly over the patient's nose or nose and mouth. The headgear is available in a range of sizes suitable for a pediatric population and to match the sizes of the nasal and full-face masks 20, 40. The headgear 30 comprises a cap 31, which extends from a peak 32 at the forehead to a neck edge 33 to cradle the back of the patient's head. A plurality of straps 34 extend from the headgear 30 and are attached to the raised buttons 90 on each mask shell 21, 41.

Preferably, a single strap 35 extends from the peak 32 of the cap 31, located at the forehead to the top 28, 46 of each mask 20, 40 and straps 36a, 36b extending outwards from each side 37, 38 of the cap 31 at the neck edge 33, in opposing directions, so as to attach to the sides 29, 47 of each mask 20, 40.

Preferably, as shown in FIGS. 9a and 9b, each strap 35, 36a, 36b comprises an elongate body 100 attached to the cap 31 at a first end 101 and having a key slot 102 formed in a second end 103 for fitting over the raised buttons 90 on each mask 20, 40 and locking into place. Each key slot 102 comprises a first hole 104 sized to fit the head 91 of the button 90 and a second smaller hole 105 extending from the first hole 104 towards the second end 103 of the strap 100. The second hole 105 is sized so as to receive and firmly retain the shank 92 of the button 90, when the first hole 104 is placed over the head 91 of the button 90 and the strap 100 is pulled into tension to engage the shank 92 in the second hole 105.

In a preferred embodiment, as shown in FIG. 9b, a separate end piece 106 having the key slot 102 formed therein is attached to the second end 103 of the strap body using a strip of hook and loop fastener 107, such as Velcro™, so as to permit adjustment in a length of the straps 100.

An opening 108 is formed at a first end 109 of the end piece 106 for accepting the Velcro™ strip 107. The slot 105 is formed extending toward a second end 110 of the end piece 106. The Velcro™ strip 107 is threaded through the opening 108 and is attached to the strap 100 at a position which provides optimum fit of the headgear 30 and mask 20, 40 to the patient. The length of the straps 100 are therefore not adjusted each and every time the mask 20, 40 is removed and replaced on the patient. The mask 20,40 is simply removed or replaced on the patient's face by engaging the key slots 102 from the buttons 90 on the mask 20, 40. In this way, the headgear 30 and mask 20, 40 can be more easily placed on a sleeping patient, without arousing them. Further, this assures that the mask 20, 40 is positioned optimally no matter where or in what position the patient has fallen asleep.

Optionally as shown in FIGS. 1 and 9a, a chin strap 120 is attached to the headgear 30 to minimize or prevent opening of the patient's mouth during therapy and thus minimize mouth leaks during use of a nasal mask 20. A strip 121 of Velcro™ is placed from side 37 to side 38 at a top 122 of the cap 31. Corresponding strips of Velcro™ 126 (only one shown) are placed on first and second ends 123, 124 of the chin strap 120. When required, the chin strap's first end 123 is simply attached to the Velcro™ strip 121 on one side 37, 38 of the cap 31, the chin strap 120 is positioned at the patients chin and the second end 124 is attached to the Velcro™ strip 121 at the cap's other side 38.

Preferably, the chin strap 120 is formed having an oval cup-shaped chin rest 125 positioned intermediate the chin strap's first and second ends 123, 124 for cradling the patient's chin. The chin rest 125 is preferably slightly padded for additional comfort.

Having reference to FIGS. 1–4 and 9a, a pair of ears 130, are attached to the headgear 30 which are usually selected to be consistent with the caricature 200 on the mask shell 21,41. The addition of ears 130 to the headgear 30 further improves compliance. Further, novelty is playfully added by using a variety of ears, regardless of the mask selection. Preferable the ears 130 are attached to the headgear 30 using small strips of Velcro™ 131.

EXAMPLE 1

Having reference to FIG. 3, three nasal masks, each having a predetermined size suitable for therapy over the size range of pediatric patients, are shown. The mask shells are ovoid in shape and concave in profile and range in size, the particular sizes being approximately; a small mask, having a height of 5 cm and a width of 4.5 cm at its widest portion; a medium mask having a height of 5.25 cm and a width of 5 cm at its widest portion; and a large mask having a height of 5.75 cm and a width of 5 cm at its widest portion. The masks display caricatures of different animal faces, each face an arbitrary yet consistent size indicator representing the size of mask, for ease of identification and to improve patient compliance. The small mask is a pig, the medium mask is a tiger and the large mask is a dog.

Similarly, as shown in FIG. 4, a full-face mask is provided in two sizes, small and large. The small size is designated as an elephant and the large size is designated as a zebra to improve patient compliance. The small full-face mask is 8 cm in height, 3 cm in width at the top and 6.5 cm at its widest where it covers the patient's mouth and the large mask is 9 cm in height, 3 cm in width at the top and 8 cm at it's widest.

Each shell has a lip about a periphery under which a removable cuff is secured. The cuffs are available with a plurality of sizes of openings for accommodating the patient's nose or nose and mouth so as to provide an optimum fit for the individual patient. The cuff sizes are represented in Table 1:

TABLE 1

CUFF SIZES

| Size Nasal Masks | Height (cm) | Width (cm) | Size Full-face masks | Height (cm) | Width (cm) |
|---|---|---|---|---|---|
| Small | 2.0 | 2.0 | Small-standard | 6.0 | 4.0 |
| Small-wide | 2.0 | 2.3 | Large-standard | 7.0 | 4.5 |
| Medium | 2.2 | 2.3 | Large-wide | 7.0 | 5.0 |
| Medium-wide | 2.2 | 2.5 | | | |
| Large | 2.5 | 2.5 | | | |
| Large-wide | 2.5 | 2.8 | | | |

Preferably, the shell and cuffs and all related tubing are manufactured to be latex-free. This is of particular importance to those patients, such as the spina bifida patients who are on "latex precaution" because of the danger of anaphylaxis. Repeated surgery and other interventions make this group of patients particularly susceptible to latex sensitivity.

Nasal mask sizes, in the series as shown, do not vary by more than 0.5 cm in width or 0.75 cm in height. Similarly the full-face masks only vary by 1.5 cm in width and 1 cm in height. Thus, the use of animal faces to designate the size ensures that the therapist is able to readily select the right size for the patient without repeated trial and error sizing.

A further advantage of the animal face size indicators is that the patient is more likely to view the mask as a fun item rather than a medical intervention, more like the pediatric oxygen device taught in U.S. Pat. No. 5,690,096 to Burch. Burch's device is a plaything, fit with a plurality of oxygen ports, which allow the patient to interact with the plaything while maintaining a flow of oxygen when placed near the mouth and nose.

Headgear is provided to position the mask correctly over the patient's nose or nose and mouth during sleep. The headgear is also available in a plurality of sizes, matched to the masks, to fit a range of pediatric sizes. To further enhance size selection and compliance, the headgear is colored or marked to match the appropriate sized mask. Preferable, the headgear is made from lightweight breathable natural materials, such as cotton, to reduce sweating.

Optionally, other aspects such as ears are added to the headgear in keeping with the mask face in order to further improve compliance. For example, a small pig mask would usually be accompanied by headgear in the same color as the mask and having a set of pig ears attached to it. The tiger headgear would be made of a fabric having a tiger stripe pattern and a pair of tiger ears attached thereto.

Preferably the ears are removable, such as attached using Velcro™, to permit easy cleaning and further, easy removal, if the ears become an obstruction during other intervention, or if the patient would prefer.

The advantages of the current pediatric mask system, which Applicant has not found in the prior art include:
improved compliance by pediatric patients due to psychological acceptance of the mask as a plaything;
improved therapeutics;
improved comfort; and
improved efficiency for the care professional; and
a more efficient use of expensive resources.

The embodiments of the invention in which and exclusive property or privildge is claimed are defined as follows:

1. A system for improving compliance in a pediatric population for the use of ventilation masks and headgear and providing size recognition comprising:

a plurality of masks and headgear of predetermined sizes so as to fit a range of pediatric patients; and a size indicator being a predetermined visage of a caricature represented on each of the plurality of masks, each caricature being predetermined to represent one of each of the plurality of predetermined sizes.

2. The system as described in claim 1 wherein each mask further comprises:
   a concave shell having
   at least one flexible cuff attached about a periphery of the shell and having an opening for receiving a patients nose or nose and mouth;
   a port in the shell for receiving a tubing for attachment to a ventilation device;
   at least one exhalation port; and
   means for attachment to a headgear.

3. The system as described in claim 2 wherein the shell further comprises at least one other port having a removable cap.

4. The system as described in claim 3 wherein the headgear further comprises a chin strap so as to prevent mouth leaks.

5. The system as described in claim 1 wherein the headgear comprises:
   a cap; and
   a plurality of straps, each strap being attached to the headgear at a first end and having means for attachment to the mask at a second end.

6. The system as described in claim 5 wherein the means of attachment of the headgear straps to the mask comprise:
   a plurality of raised buttons located at the periphery of the mask shell; and
   a shaped slot formed in the second end of each strap for retaining the button.

7. The system described in claim 6 further comprising:
   a first headgear strap is attached from a peak in the cap to a top of the mask shell so as to not impair vision; and
   second and third headgear straps extending outwards in opposing directions from a neck edge of the cap to attach to buttons on a first and second side of the mask shell.

8. The system as described in claim 5 further comprising a matching aspect, further identifying the caricature, attached to the headgear.

9. The system as described in claim 8 wherein the matching aspect is ears.

10. The system as described in claim 5 further comprising ears attached to the headgear.

11. The system as described in claim 10 wherein the ears match the caricature.

12. The system as described in claim 1 wherein the caricature on the mask is an animal face.

13. The system as described in claim 12 wherein there are two exhalation ports, the exhalation ports forming part of a nasal feature of the animal face.

14. A system for improving compliance in a pediatric population for the use of ventilation masks and headgear and providing size recognition comprising:
   a plurality of masks and headgear of predetermined sizes so as to fit a range of pediatric patients wherein:
   the mask further comprises a concave shell; at least one flexible cuff attached about a periphery of the shell and having an opening for receiving a patients nose or nose and mouth; a port in the shell for receiving tubing for attachment to a ventilation device; at least one exhalation port; and means for attachment to the headgear; and
   the headgear comprises a cap and a plurality of straps having means for attachment to the mask; and
   a size indicator being a predetermined visage of a caricature represented on each of the plurality of masks, each caricature being predetermined to represent one of each of the plurality of sizes.

15. The system as described in claim 14 wherein the mask shell further comprises at least one other port having a removable cap.

16. The system as described in claim 14 wherein the means of attachment of the headgear straps to the mask comprise:
   a plurality of raised buttons located at the periphery of the mask shell; and
   a shaped slot formed in an end of each strap for retaining the button.

17. The system as described in claim 14 further comprising:
   a first headgear strap is attached from a peak in the cap to a top of the mask shell so as to not impair vision; and
   second and third headgear straps extending outwards in opposing directions from a neck edge of the cap to attach to buttons on a first and second side of the mask shell.

18. The system as described in claim 14 wherein the headgear further comprises a chin strap so as to minimize mouth leaks.

19. The system as described in claim 14 wherein the caricature on the mask is an animal face.

20. The system as described in claim 19 wherein there are two exhalation ports, the exhalation ports forming part of a nasal feature of the animal face.

21. The system as described in claim 14 further comprising a matching aspect, further identifying the caricature, attached to the headgear.

22. The system as described in claim 21 wherein the matching aspect is a set of ears.

23. A mask for improving compliance in a pediatric population and providing size recognition for use with ventilation therapy, the mask comprising:
   a concave shell having an outer periphery and having a s selected from a plurality of predetermined sizes;
   at feast one flexible cuff attached to the shell about the periphery and having an opening so as to receive a patient's nose or nose and mouth;
   an inflatable cuff attached within the periphery of the shell and within the at least one flexible cuff;
   at least one port in the shell for receiving tubing;
   at least one exhalation port; and
   a size indicator, the indicator being one of a plurality of caricatures predetermined to represent one of the plurality of predetermined sizes.

24. The mask as described in claim 23 wherein the caricature is an animal face.

25. The mask as described in claim 24 wherein there are two exhalation ports, the exhalation ports forming part of a nasal feature of the animal face.

26. The mask as described in claim 23 wherein the at least one flexible cuff is removable and replaceable.

27. The mask as described in claim 23 further comprising at least one additional port having a cap so as to administer additional inhalation gases or monitor exhalation gases.

28. The mask as described in claim 23 further comprising a compression slip ring to retain the tubing to the shell.

29. The mask as described in claim 23 wherein the shell is transparent.

30. A mask for use with ventilation therapy, the mask comprising:
- a concave shell having an outer periphery;
- a flexible exterior cuff attached to the shell about the periphery and having an opening so as to receive a patient's nose or nose and mouth;
- an inflatable interior cuff attached to the shell end positioned inside the exterior cuff, the inflatable cuff further comprising a valve port extending the rough the shell and in fluid communication with the inflatable cuff;
- at least one exhalation port; and
- at least one port in the shell for receiving tubing.

31. The mask as described in claim 30, the exterior cuff being removable, the mask further comprising:
- a lip formed about the periphery of the shell for forming a space between the shell and the lip; and
- the exterior cuff having a flexible compressible edge, the edge sized sightly larger than the space so as to be fit in the space when compressed and retained therein.

32. The mask as described in claim 30 further comprising at least one additional port having a cap so as to administer additional inhalation gases or monitor exhalation gases.

* * * * *